United States Patent [19]

Sano

[11] 4,277,803
[45] Jul. 7, 1981

[54] AUTOMATIC PRODUCT CHECKING SYSTEM

[75] Inventor: Yasukazu Sano, Kawasaki, Japan

[73] Assignee: Fuji Electric Co., Ltd., Tokyo, Japan

[21] Appl. No.: 149,261

[22] Filed: May 12, 1980

[51] Int. Cl.³ ............................................. H04N 7/18
[52] U.S. Cl. ................................... 358/106; 356/237
[58] Field of Search ..................... 358/106, 107, 101; 356/237

[56] References Cited

U.S. PATENT DOCUMENTS 3,922,093 11/1975 Dandliker .............................. 358/106
4,139,306 2/1979 Norton ................................... 358/106

*Primary Examiner*—Howard Britton
*Attorney, Agent, or Firm*—Bruce L. Birchard

[57] ABSTRACT

The surface condition of a product being checked is determined by viewing the product with a raster-scanned television camera, or its equivalent and, on a horizontal-line-by-horizontal-line basis detecting the number of points in the video envelope which have a zero slope (a derivative of "zero") and, from such information generating a reject signal if the number of points exceeds one.

10 Claims, 10 Drawing Figures

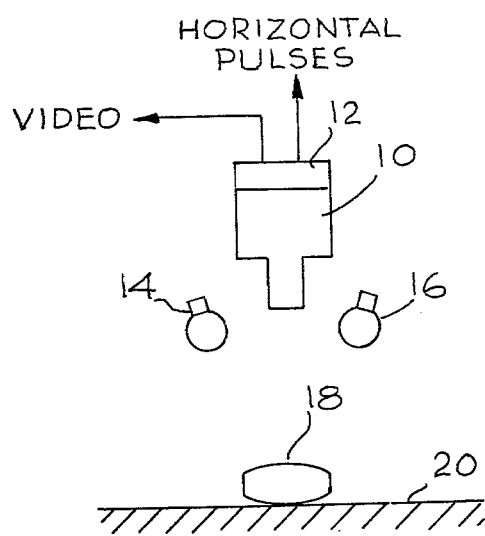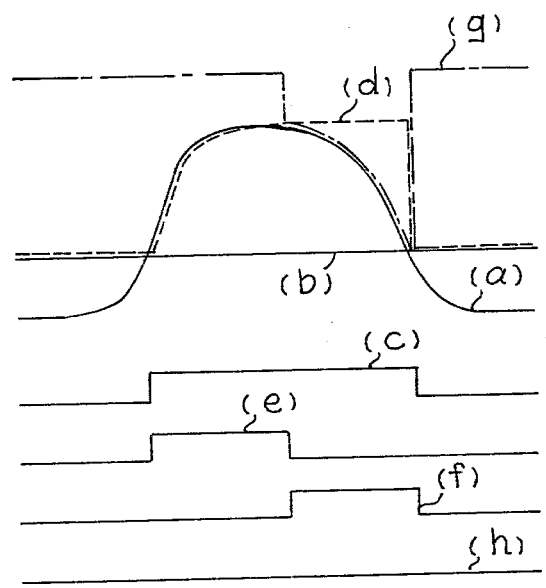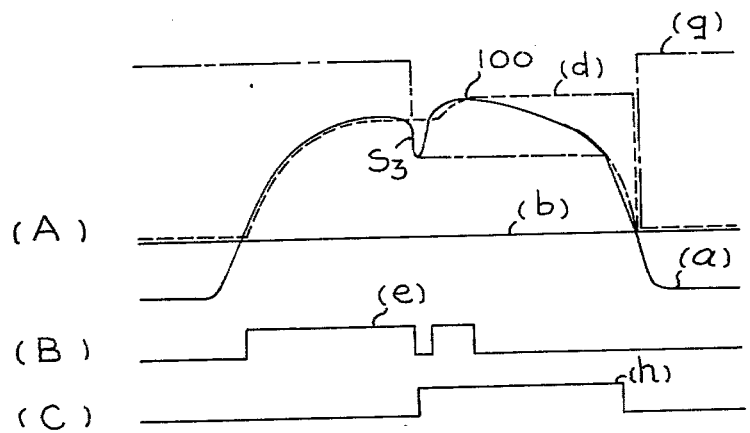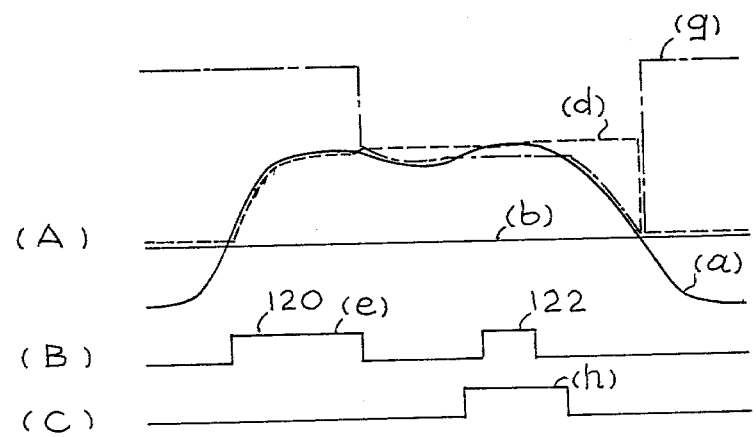

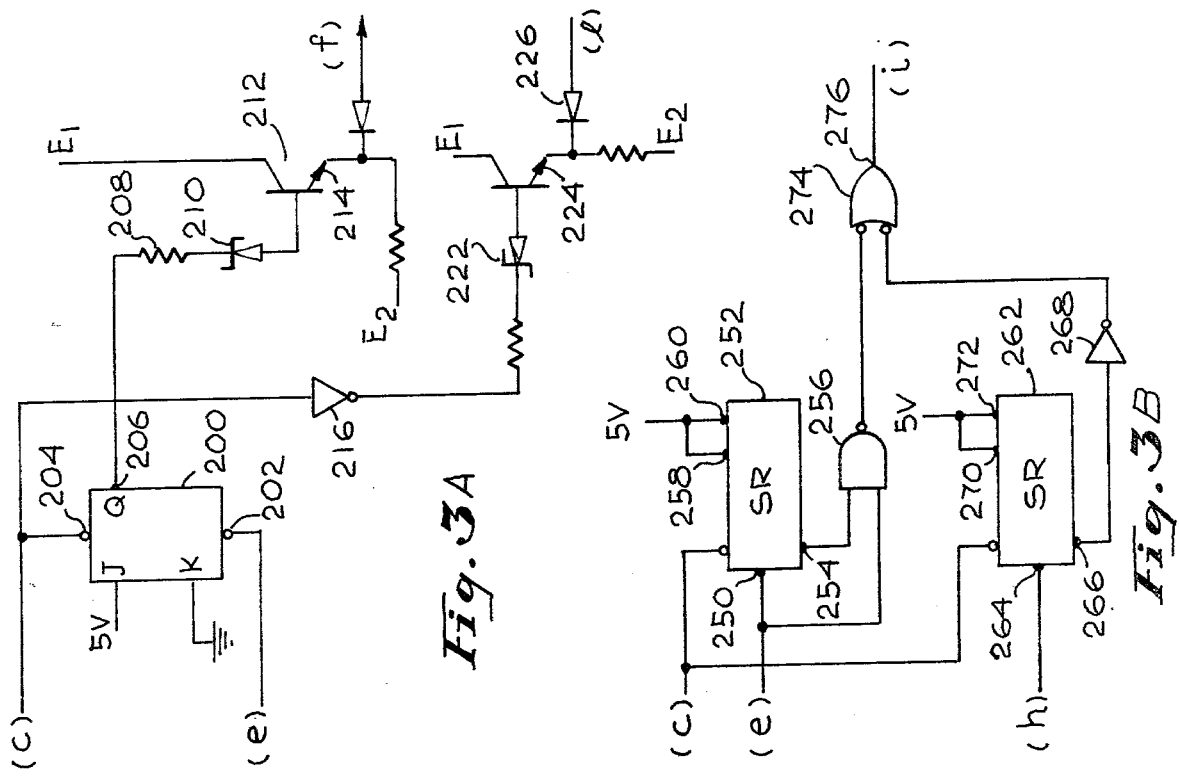
Fig. 3A
Fig. 3B
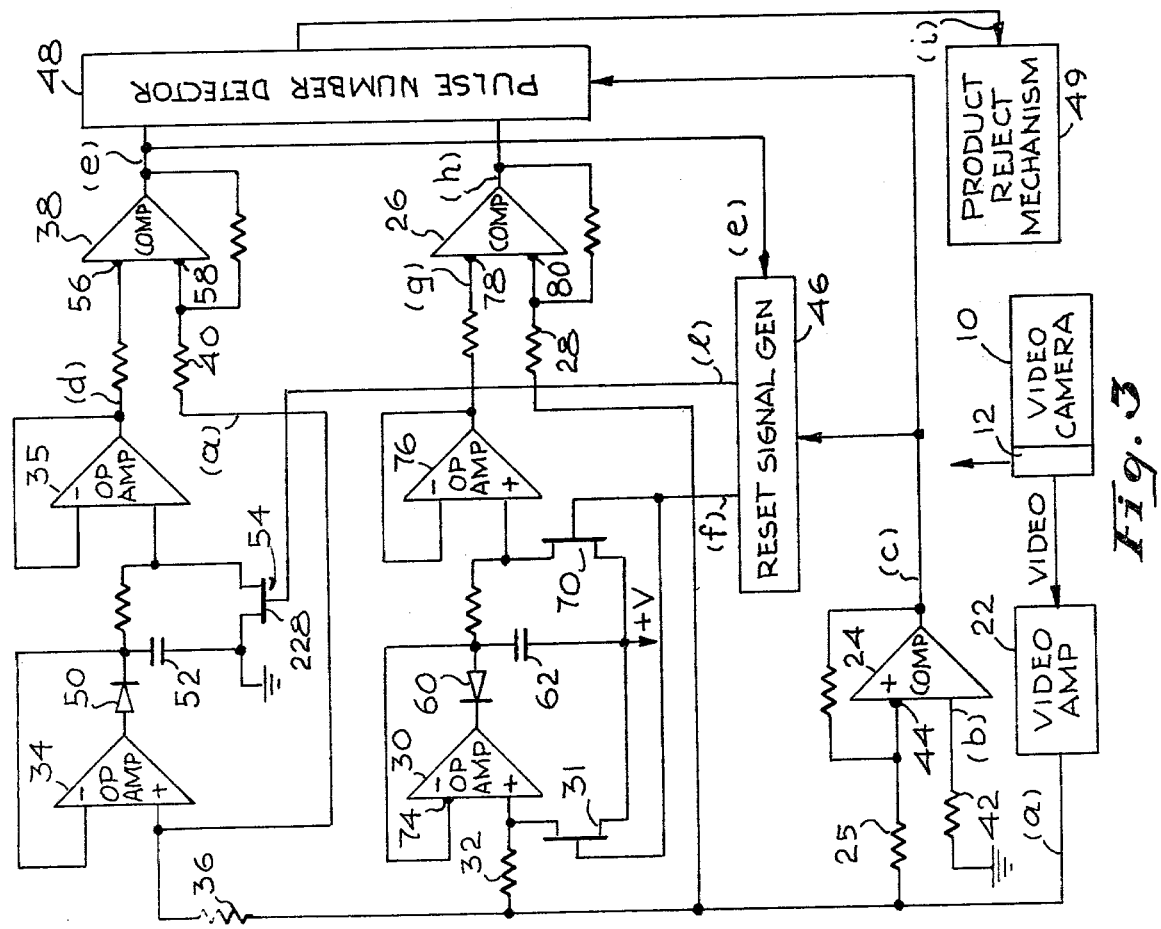
Fig. 3

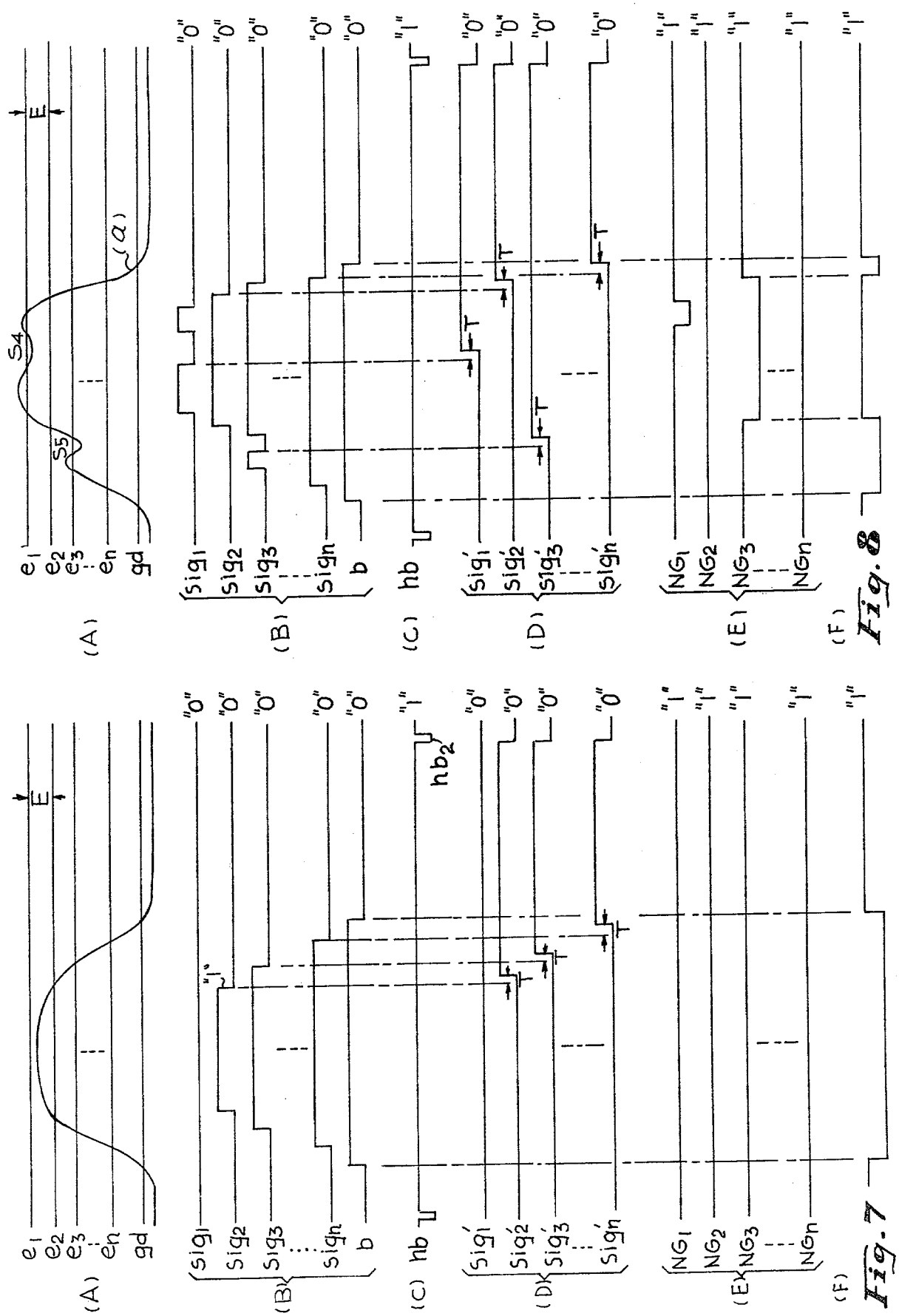

AUTOMATIC PRODUCT CHECKING SYSTEM

BACKGROUND OF THE INVENTION

1. Field of the Invention

This invention relates to automatic product checking equipment and more particularly to such equipment useful in checking the surface conditions of such a product, for example, a pill.

2. Prior Art

The use of a video envelope corresponding to a viewed object to check the acceptability of such an object or product has, in the past, utilized a fixed reference voltage, for example a standard reference cell, with which the amplitude of the envelope is compared or, alternatively, a floating reference produced by attenuating and delaying the video envelope and comparing it with the original envelope. Both of such comparison systems suffer from insensitivity to minor video envelope changes which arise when a minor, but objectionable defect, such as a scratch, appears on the surface of the product, for example a medicinal pill.

Therefore, it is a general object of this invention to overcome the disadvantages of the prior art devices, such as those set forth hereinbefore.

It is a further object of this invention to provide an improved, highly sensitive method and apparatus for checking the surface conditions of a product to determine whether that product should be accepted or rejected.

SUMMARY OF THE INVENTION

The product being checked is viewed by a video camera which has raster scanning of its photo-sensitive surface. The video envelope developed by the camera is analyzed on a horizontal line-by-horizontal line basis and the amplitude of the video signal along each horizontal line is compared with a threshold level (derived from the video envelope) for that line. If the video signal for each line shows more than one zero-slope condition, an improper change in direction, or dip, in the video curve is indicated, further indicating a defect in the surface of the product.

BRIEF DESCRIPTION OF THE DRAWINGS

The present invention and its method of operation can best be understood by referring to the description which follows, taken in connection with the related drawings, in which:

FIG. 1 is a schematic diagram of the basic system utilized in this invention;

FIG. 2 is a graphical representation of a signal from the system of FIG. 1;

FIG. 3 is a schematic diagram of a first embodiment of this invention;

FIG 3A is a schematic diagram of a portion of the circuit of FIG. 3;

FIG. 3B is a schematic diagram of an additional portion of the circuit of FIG. 3;

FIG. 4 is a graphical representation of the signal from the circuit of FIG. 6 under a first product defect condition;

FIG. 5 is a graphical representation of signals out of the circuit of FIG. 3 under a second product defect condition;

FIG. 7 is a graphical representation of signals into and out of the circuit of FIG. 6 under a first set of product conditions; and, FIG. 8 is a graphical representation of signals into and out of the circuit of FIG. 6 under a second set of product conditions.

DETAILED DESCRIPTION OF THE PREFERRED EMBODIMENTS

Figure 6:
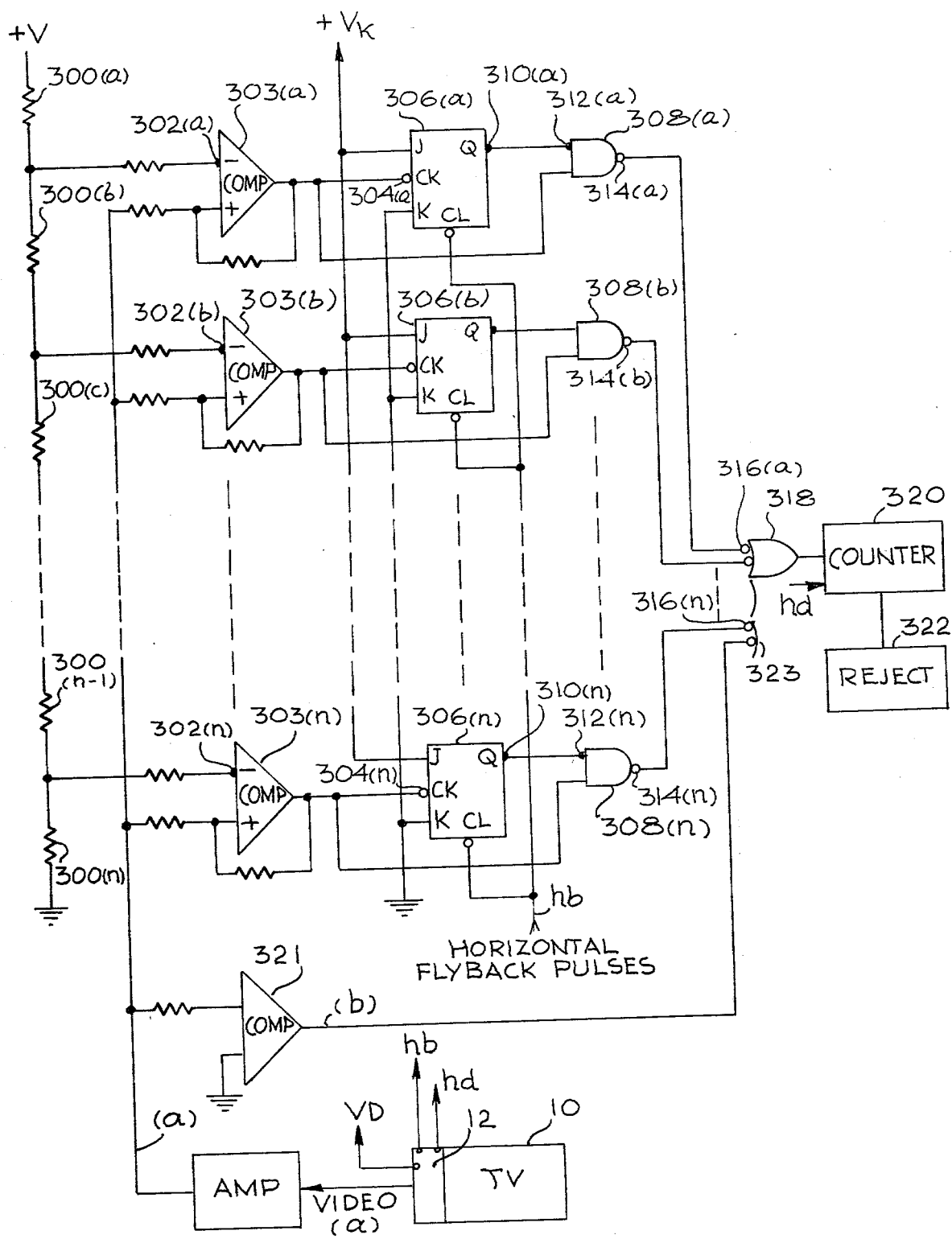
FIG. 6 is a schematic diagram of a second embodiment of this invention.

In FIG. 1, video camera 10 may be of the industrial type having horizontal and vertical, or "raster" scanning. The horizontal and vertical scanning circuits are well known and need not be described here. The photoelectric converter in the camera may be a vidicon. A synch stripping circuit 12 is provided to separate video and synch signals for use as described hereinafter.

Lamps 14 and 16 are provided to illuminate product 18 fully, assuring that there are no shadows on it. Product 18, the surface of which is to be checked for defects, rests on a smooth support 20, which may be a conveyor belt, in which case lamps 14 and 16 may be strobe lamps. The color of support 20 should be such as to give a good light-contrast ratio with product 18.

The processing circuits and results are best seen in FIGS. 2 and 3. In FIG. 3, the video signal from camera 10 is amplified in amplifier 22 and applied to comparator 24 thru resistor 25 and is applied to comparator 26 through resistor 28.

The amplified video signal (a) is also applied to operational amplifier 30 and FET 31 through resistor 32. The same signal (a) is applied to operational ammplifier 34 thru resistor 36 and to comparator 38 thru additional resistor 40.

Biasing resistor 42 sets the level (b) at which comparator 24 puts out a "one" signal in response to the application of video signal (a) to its terminal 44. That "one" signal is designated "c" in FIG. 2 and is applied to Reset Signal Generator 46 and to Pulse Number Detector 48.

The setting of level (b) essentially determines the portion of curve (a) that is analyzed. The combination of operational amplifier 34, diode 50 and condenser 52 results in setting an upper threshold voltage (d) at the maximum amplitude of curve (a) as long as FET 54 remains open. That upper threshold voltage (d) appears at terminal 56 of comparator 38 and acts as a reference voltage. As has been indicated, video signal (a) is applied to the other input terminal 58 of comparator 38. As long as signal (a) equals or exceeds signal (d), the output signal (e) from comparator 38 is a "one". As soon as signal (a) falls below signal (d), the output (e) from comparator 38 falls to "zero" as can be seen in FIG. 2. The falling of curve (a) occurs following a zero slope (derivative equals zero) for curve (a). Pulse Number Detector 48 counts the number of pulses per horizontal scanning line and if the number exceeds one, a reject signal (i) is generated.

Operational amplifier 30, in combination with diode 60 and condenser 62 set the minimum threshold level for the analysis of signal (a). During this threshold setting process FET's 31 and 70 are held in an open state by a signal from Reset Signal Generator 42, the details of which will be set forth more clearly in connection with FIG. 3A.

As can be seen from FIG. 3 condenser 62 is connected to +V on one side and to the minus terminal 74 of op amp 30, on the other side. With this connection, the output signal from the lower threshold circuit is curve (g) of FIG. 2 which begins at the zero slope point on curve (a) and continues downwardly along with curve (a) until the analysis is cut off at the end of curve (c), FIG. 2. Operational amplifier 76 applies signal (g) to the minus terminal 78 of comparator 26. Video signal (a) is applied to the positive terminal 80 of comparator 26. When signal (a) is equal to or less than signal (g) the output signal (h) from comparator 26 is zero. If (a) exceeds (g) the output from comparator 26 is a "one". As can be seen from both curves (a) and (g) in FIG. 2, curve (a) never exceeds curve (g) and hence output curve (h) is always a "zero."

The contrary is true in the signal of curve (a) of FIG. 4. The dip in video signal at $S_3$ shows a scratch or other defect in the surface of product 18.

The upper threshold curve (d) exceeds curve (a) at $S_3$ causing comparator 38 to output a "zero" during the period between the zero slope preceding $S_3$ and the time when curve (a) rises to intersect curve (d). Another zero slope occurs at point 100 and signal (a) falls below signal (d) to cause comparator 38 to output another "zero." The resulting signal (e) in FIG. 4 shows two pulses which are counted in pulse number detector 48. The falling of curve (g) below curve (a) causes comparator 26 to output a "one" for the duration of that condition and signal (h) of FIG. 4 results. It, too, is fed to detector 48 and counted. The number of pulses being greater than one, a reject signal (i) will be developed for application to product reject mechanism 49.

Similarly in FIG. 5, signal (a) falls below upper threshold (d) twice producing two pulses 120 and 122. Signal (a) exceeds the lower threshold signal (g) once, producing pulse (h). Those pulse will be counted in detector 48. Thus, even though the variations in video envelope (a) are only slight they will produce output pulses which can be counted to indicate surface defects in product 18. A high degree of quality control is thus achievable.

At the end of the analysis, as indicated by the trailing edge of pulse (c) Reset Signal Generator 46 turns on FET's 31, 54 and 70 and condenser 52 and 62 are discharged leaving the system ready for the analysis of the video envelope corresponding to the next horizontal scanning line.

Purely by way of example, operational amplifiers 30, 34, 35 and 76 may be type CA 3140A available from RCA. Comparators 24, 26 and 38 may be type μPC 71A available from Nippon Electric Co., Ltd. Diodes 50 and 60 may be type 1S953 available from NEC. Transistors 31, 54 and 70 may be type 2SK 30A available from Toshiba.

The fashion in which Reset Signal Generator 46 operates can best be understood from FIG. 3A. In FIG. 3A, flip-flop 200 has clock terminal 202 which receives signal (e) of FIGS. 2 and 3. Clear terminal 204 receives signal (c) out of comparator 24. When signal (e) changes from a logic "1" to a logic "0", with signal (c) in a "1" state, the $\overline{Q}$ output at terminal 206 switches from a "1" to a "0". If signal (c) becomes a "zero" the $\overline{Q}$ output at terminal 206 becomes a "1". Thus an inverted (f) signal is derived.

For switching FET's 31 and 70 the swing of emitter voltage of transistor 212 by $E_1-E_2$ (when $E_1 \geq +V$ and $E_2 < 0$) is produced by applying the inverted (f) signal from terminal 206 of flip-flop 200 to the base of transistor 212 thru Zener diode 210. The voltage swing at emitter 214 becomes signal (f) applied to the gates of FET's 31, 70. Signal (f) turns off FET's 31, 70 for its duration permitting signal (g) to follow signal (a) in a downwardly direction and clamping the voltage on condenser 62 at the lowest level of signal (a) before a rise thereof.

The line signal (1) is derived from the (c) signal which is inverted in inverter 216 and applied to base 218 of transistor 220 thru Zener diode 222. The voltage swing of emitter 224 (which is an inverted (c) signal) is fed thru diode 226 to gate 228 of FET 54 and cuts it off for the duration of signal (c), thus permitting condenser 52 to charge for the duration of the video signal above base level (b) which is set above the noise level. At the end of signal (1) FET 54 turns on and discharges condenser 52. At the end of signal (f) FET's 31 and 70 turn on discharging condenser 62.

The operation of Pulse Number Detector 48 can best be understood by reference to FIG. 3B. Signal (e) of FIGS. 2 and 3 is applied to clock terminal 250 of shift register 252 which may be an SN 74164. The output from terminal 254 of shift register 252 is supplied, along with signal (e) to Nand gate 256. If signal (c) is a "one" and signal (e) contains more than one pulse than Nand gate 256 produces an output "zero." Data terminals 258 and 260 are provided with a voltage representing a logic "one."

Similarly, another shift register 262 is connected to receive the signal (h) at its clock terminal 264. Its ouput is produced from its terminal 266 and is inverted by an inverter 268. If the signal (c) has the logic value "1" and the signal (h) includes one pulse or more, then the inverter 268 produces an output having the logic value "0". Data terminals 270 and 272 here are also supplied with a signal representing the logic value "1".

Consequently, if a signal (e) with two or more pulses or a signal (h) with a pulse or more is supplied when the signal (c) has the logic value of "1", then a NOR-gate 274 produces a logic "one" as signal (i) at its output 276 for the duration of the time signal (c) remains in the logic value "1". When the signal (c) turns back to a logic "0", the output (i) also returns to the logic value of "0". Thus a rejection signal (i) is obtained for application to a rejection mechanism and ejection of the defective product 18.

In FIG. 6, resistors 300(a) thru 300(h) form a voltage divider which sets—terminals 302(a) thru 302(n) at different voltage levels so that comparators 304(a) thru 304(n) put out a logic "one" at respectively different levels of video signal (a) which is applied to the "+" terminals of respective ones of the comparators 303(a) thru 303(n). Essentially, signal (a) is sliced at different voltage levels and analyzed for multiple pulse outputs from the respective comparators for each level, indicating changes in slope of the video signal and, ultimately, discontinuities or defects in the object being checked. The output signals from comparators 303(a) thru (n) are fed to the clock input terminals 304(a) thru (n), respectively, of "J-K" flip-flops 306(a) thru (n), respectively.

Those flip-flops are cleared at the end of every horizontal scanning line in camera 10 by horizontal flyback pulses hb taken from synch separator 12 and applied to the clearing terminals (CL) of flip-flops 306(a) thru (n), respectively.

The output signals from comparators 303(a) thru (n) are also fed to input terminals 307(a) thru (n) of NAND gates 308(a) thru (n), respectively.

The "Q" output terminals 310(a) thru (n) of flip-flops 306(a) thru (n) are connected to respective remaining input terminals 312 (a) thru (n) of NAND gates 308 (a) thru (n), respectively.

The output terminals 314 (a) thru (n) of NAND gates 308 (a) thru (n) are connected to respective multiple input terminals 316 (a) thru (n) of NOR gate 318.

Video signal (a) is also applied to comparator 321 which outputs a "1" when signal (a) exceeds a background noise level (gd), FIG. 7.

The output signal from comparator 321 is applied to input terminal 323 of NOR gate 318. Output pulses from NOR-gate 318 are counted in counter 320 and if the number of pulses exceeds one a reject signal is sent to rejection apparatus 322.

The fashion in which the appartus of FIG. 6 operates can best be understood from the diagrams of FIGS. 7 and 8. In FIG. 7A, the reference voltages at terminals 302(a) thru (n) are represented by voltages $e_1$ thru $e_N$, respectively. The difference between successive reference levels is represented by voltage E, FIG. 7A. The video signal (a) is analyzed for zero slopes at multiple levels above the noise blanking level (gd).

The output signals from comparators 303(a) thru (n) are designated $sig_1$ thru $sig_n$ in FIG. 7B. As can be seen from FIG. 7B, video signal (a) does not reach level $e_1$ and, thus, comparator 303(a) does not output a "one" at any time. At level $e_2$ comparator 303(b) outputs a "one" during the time signal (a) equals or exceeds $e_2$. That is "$sig_2$" in FIG. 7B.

Similarly, for comparators down to comparator 303(n) a single output pulse or "one" occurs for each period between horizontal flyback pulses hb (FIG. 7(C)). The Q outputs from flip-flops 306(a) thru (n) are presented as "$sig'_1$" thru "$sig'_n$" in FIG. 7D. As can be seen from FIG. 7D, since $sig_1$ is a "zero", $sig'_1$ is also a "zero." The falling or trailing edge of the "1" in signal "$sig_2$" switches flip-flops 306(b) to a "one" state after a delay time "T" set for the "Q" output of flip-flop 306(b). At the leading edge of flyback pulse "$hb_2$", flip-flop 306(b) is cleared and $sig'_2$ returns to a logic "zero" state. Similarly, "$sig'_3$" thru "$sig'_n$", FIG. 7D comprise a single pulse or "one". The signals from flip-flops 306(a) thru (n), when applied to NAND gates 308(a) thru (n), along with the output signals from comparators 306(a) thru (n), produce the output signals ($NG_1$ thru $NG_n$) shown in FIG. 7E. The output signals $NG_1$ thru $NG_n$ are all seen to be logic "ones" in FIG. 7E.

When the NG signals are applied to multiple input NOR gate 318 along with the output signal (b) from comparator 321 the single output pulse of FIG. 7F occurs indicating no defects in the object being checked. Thus, no reject signal is sent from counter 320 to reject apparatus 322 in FIG. 6.

If the product has surface defects, for example two such defects, the curves of FIG. 8 apply. In FIG. 8(A), video signal (a) is seen to have two dips ($S_4$ and $S_5$) in it, indicating two scratches, impurities or other surface defects in the product being checked. Signal (a) crosses reference level e, four times, twice with a positive slope and twice with a negative slope. Stated another way, signal (a) rises above reference level e, twice and falls below it twice. The result is that "$sig_1$" has two "one" states, as shown in FIG. 8(B). Flip-flop 306(a) is turned on by the first falling edge in "$sig_1$" after a delay time "T", to produce "$sig_1$", FIG. 8D. Dip "$S_5$" in signal (a) produces, from comparator 306(c), the multiple "ones" shown in "$sig_3$" of FIG. 8(B). The Q output of flip-flop 306(c) is shown as "$sig'_3$" which becomes a "one" at the first falling edge in "$sig_3$" and continues until the horizontal flyback signal hb clears flip-flop 306(c). The output of NAND gate 308(a) shows one pulse, a "zero", corresponding to the rise in signal (a) following dip $S_4$. The output curve for NAND gate 308(c) (FIG. 8(E)) shows one pulse, a "zero". All of the NAND outputs when applied to NOR gate 318, produce the signal shown at FIG. 8(F) which has two pulses (both "zeroes") in it. Those pulses are counted in counter 320 and, since the number of pulses exceeds one a "reject" signal will be generated and sent to reject mechanism 322.

Purely by way of example, comparators 303(a) thru (n) may be type μPC71 A available from Nippon Electric Co., Ltd. Flip-flops 306(a) thru (n) may be type SN74107 available from Texas Instruments. NAND-gates 308(a) thru (n) may be type SN7400 available from Texas Instruments. Multiple input NOR-gate 318 may be a type SN7430 available from Texas Instruments. Shift registers 252 and 262 may be type SN74164 available from Texas Instruments.

While particular embodiments of the present invention have been shown and described, it will be obvious to those skilled in the art that changes and modifications may be made without departing from my invention in its broader aspects, and, therefore, the aim of the appended claims is to cover all such changes and modifications as fall within the true spirit and scope of my invention.

What is claimed is:

1. The method for checking the surface condition of a product which method includes the following steps:
   generating a video signal representing at least a portion of the surface of the product;
   counting the number of zero-slope conditions in said video signal; and,
   generating a defect signal if the number of such zero-slope conditions exceeds one.

2. The method according to claim 1 in which said counting of the number of zero-slope conditions is performed at a plurality of predetermined reference levels in said video signal.

3. The method according to claim 1 which includes the additional step of rejecting said product in response to said defect signal.

4. The method according to claim 1 which includes the additional steps of generating from said video signal an upper threshold signal and a lower threshold signal; detecting each cross-over between said video signal and said upper threshold signal, in a positive direction, and each cross-over between said video signal and said lower threshold signal, in a negative direction; and, generating said defect signal if the number of such cross-over exceeds one.

5. Apparatus for detecting surface defects in a product, including:
   video-signal generating means for generating a video signal representing at least a portion of the surface of said product;
   detecting means coupled to said video-signal generating means for detecting any zero slope condition in said video signal;
   counting means coupled to said detecting means for counting the number of zero-slope conditions detected; and,
   defect-signal generating means coupled to said counting means for generating a defect signal in response to a count of more than one zero-slope condition in said video signal.

6. Apparatus according to claim 5 in which said detecting means includes an upper-threshold-signal generating means and a lower-threshold-signal generating means; upper comparison means coupled to said upper-threshold-signal generating means and to said video-signal generating means and responsive to a cross-over between said video-signal and said upper-threshold signal, in a positive direction, to produce an output pulse;

lower comparison means coupled to said lower-threshold-signal generating means and to said video-signal generating means and responsive to a cross-over between said video signal and said lower-threshold signal, in a negative direction, to produce an output pulse; and, counting means coupled to said upper and lower comparison means, respectively, and responsive to said output pulses therefrom to produce a defect signal if the number of such output pulses exceeds one.

7. Apparatus according to claim 5 in which said detecting means includes a plurality of comparison means each having a reference terminal, a signal input terminal and an output terminal, each reference terminal being set at a predetermined fixed voltage.

8. Apparatus according to claim 5 in which said video-signal generating means generates a video raster having horizontal and vertical scanning lines and said apparatus includes, in addition, re-set means for resetting said detecting means after each horizontal scanning line in said video signal.

9. Apparatus according to claim 5 which includes, in addition, product rejection means coupled to said defect-signal generating means and responsive to a defect signal therefrom to reject said product.

10. Apparatus according to claim 8 in which said re-set means is coupled to said video signal generating means and is responsive to horizontal fly-back pulses therefrom to re-set said detecting means.

* * * * *